United States Patent
Parker et al.

(10) Patent No.: US 8,050,770 B2
(45) Date of Patent: *Nov. 1, 2011

(54) POWER EFFICIENT ELECTRICAL STIMULATION

(75) Inventors: John Parker, Roseville (AU); James F. Patrick, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 738 days.

This patent is subject to a terminal disclaimer.

(21) Appl. No.: 11/857,253

(22) Filed: Sep. 18, 2007

(65) Prior Publication Data

US 2008/0051853 A1 Feb. 28, 2008

Related U.S. Application Data

(63) Continuation of application No. 10/343,397, filed as application No. PCT/AU01/01032 on Aug. 21, 2001, now Pat. No. 7,272,446.

(30) Foreign Application Priority Data

Aug. 21, 2000 (AU) .................................. PQ9528

(51) Int. Cl.
*A61N 1/00* (2006.01)
(52) U.S. Cl. ......................................................... 607/57
(58) Field of Classification Search .................. 607/57
See application file for complete search history.

(56) References Cited

U.S. PATENT DOCUMENTS

| | | | |
|---|---|---|---|
| 4,441,202 A | 4/1984 | Tong et al. | |
| 4,515,158 A | 5/1985 | Patrick et al. | |
| 4,532,930 A * | 8/1985 | Crosby et al. | 607/57 |
| 4,611,596 A | 9/1986 | Wasserman | |
| 4,847,617 A | 7/1989 | Silvian | |
| 5,046,242 A | 9/1991 | Kuzma | |
| 5,271,397 A | 12/1993 | Seligman et al. | |
| 5,274,711 A | 12/1993 | Rutledge et al. | |
| 5,403,262 A | 4/1995 | Gooch | |
| 5,412,748 A | 5/1995 | Furuyama et al. | |
| 5,601,617 A | 2/1997 | Loeb et al. | |
| 5,609,616 A | 3/1997 | Schulman et al. | |
| 5,626,629 A | 5/1997 | Faltys et al. | |
| 5,649,970 A | 7/1997 | Loeb et al. | |
| 5,653,742 A | 8/1997 | Parker et al. | |
| 5,687,282 A | 11/1997 | Van De Kerkhof | |
| 5,776,179 A | 7/1998 | Ren et al. | |
| 5,786,439 A | 7/1998 | Van Antwerp et al. | |

(Continued)

FOREIGN PATENT DOCUMENTS

AU 2005202733 1/2006

(Continued)

OTHER PUBLICATIONS

CA Examiner's report dated May 29, 2007.

(Continued)

*Primary Examiner* — Eric D Bertram
*Assistant Examiner* — Roland Dinga
(74) *Attorney, Agent, or Firm* — Kilpatrick, Townsend & Stockton, LLP.

(57) ABSTRACT

Neural stimulation device with improved power consumption and/or effectiveness. The device is configured to recognize proposed stimuli which will be masked by earlier or simultaneous stimuli. Such masked stimuli are either deleted, or replaced by another stimuli.

22 Claims, 2 Drawing Sheets

U.S. PATENT DOCUMENTS

| | | | |
|---|---|---|---|
| 5,824,022 A | 10/1998 | Zilberman et al. | |
| 5,833,714 A | 11/1998 | Loeb | |
| 5,853,424 A | 12/1998 | Rise | |
| 5,895,416 A | 4/1999 | Barreras, Sr. et al. | |
| 5,909,497 A | 6/1999 | Alexandrescu | |
| 6,115,478 A | 9/2000 | Schneider | |
| 6,116,413 A | 9/2000 | Tabor et al. | |
| 6,198,971 B1 | 3/2001 | Leysieffer | |
| 6,230,057 B1 | 5/2001 | Chow et al. | |
| 6,304,786 B1 | 10/2001 | Heil, Jr. et al. | |
| 6,304,787 B1 | 10/2001 | Kuzma et al. | |
| 6,321,126 B1 | 11/2001 | Kuzma | |
| 6,334,072 B1 | 12/2001 | Leysieffer | |
| 6,354,299 B1 | 3/2002 | Fischell et al. | |
| 6,366,863 B1 | 4/2002 | Bye et al. | |
| 6,421,569 B1 | 7/2002 | Treaba et al. | |
| 6,463,328 B1 | 10/2002 | John | |
| 6,497,729 B1 | 12/2002 | Moussy et al. | |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,594,525 B1 | 7/2003 | Zierhofer | |
| 6,697,674 B2 | 2/2004 | Leysieffer et al. | |
| 6,751,505 B1 * | 6/2004 | Van Den Honert et al. | 607/57 |
| 6,778,040 B2 | 8/2004 | Kim | |
| 6,778,858 B1 | 8/2004 | Peeters | |
| 6,879,693 B2 | 4/2005 | Miller | |
| 6,916,291 B2 | 7/2005 | Givens et al. | |
| 7,171,272 B2 | 1/2007 | Blamey et al. | |
| 7,181,297 B1 | 2/2007 | Pluvinage et al. | |
| 7,218,971 B2 | 5/2007 | Heil, Jr. et al. | |
| 7,251,530 B1 | 7/2007 | Overstreet et al. | |
| 7,272,446 B2 * | 9/2007 | Parker et al. | 607/57 |
| 7,317,944 B1 | 1/2008 | Overstreet | |
| 7,328,151 B2 | 2/2008 | Muesch | |
| 7,822,478 B2 * | 10/2010 | Killian et al. | 607/57 |
| 2001/0050837 A1 | 12/2001 | Stevenson et al. | |
| 2002/0176584 A1 | 11/2002 | Kates | |
| 2003/0109903 A1 | 6/2003 | Berrang et al. | |
| 2003/0199950 A1 | 10/2003 | Stolz et al. | |
| 2003/0233133 A1 | 12/2003 | Greenberg et al. | |
| 2004/0098063 A1 | 5/2004 | Goetz | |
| 2004/0127968 A1 | 7/2004 | Kuzma et al. | |
| 2004/0147992 A1 | 7/2004 | Bluger et al. | |
| 2006/0004432 A1 | 1/2006 | Parker et al. | |
| 2007/0127745 A1 | 6/2007 | Gibson et al. | |
| 2009/0204177 A1 | 8/2009 | Parker et al. | |
| 2009/0292161 A1 | 11/2009 | Parker | |

FOREIGN PATENT DOCUMENTS

| | | |
|---|---|---|
| EP | 0247649 | 12/1987 |
| EP | 0282336 | 9/1988 |
| EP | 0124930 | 6/1990 |
| JP | 61001200 | 1/1986 |
| JP | 63242252 | 10/1988 |
| JP | 8501241 | 2/1996 |
| JP | 10508442 | 8/1998 |
| JP | 11-513539 T | 11/1999 |
| JP | 2000509566 | 7/2000 |
| WO | 9324176 | 12/1993 |
| WO | 9501709 | 1/1995 |
| WO | 9612383 | 4/1996 |
| WO | WO-9626673 | 9/1996 |
| WO | 9709863 A1 | 3/1997 |
| WO | 97/43871 A1 | 11/1997 |
| WO | 97/48447 | 12/1997 |
| WO | 9965276 | 12/1999 |
| WO | 0103622 | 1/2001 |
| WO | 0119304 | 3/2001 |
| WO | 0199470 | 12/2001 |
| WO | WO-0217679 | 2/2002 |

OTHER PUBLICATIONS

Nogueira et al. "A Psychoacoustic 'NofM'-Type Speech Coding Strategy for Cochlear Implants," EURASIP Journal on Applied Signal Processing, pp. 3044-3059, 2005.

Supplementary European Search Report dated Aug. 11, 2005.

First European Examiner's Report for European Application No. 01959971.1 dated dated Nov. 23, 2005.

Second CA Office Action dated Dec. 10, 2008.

Bernd Edler, Heiko Purnhagen, and Charalampos Ferekidis, ASAC—Analysis/Synthesis Audio Codec for Very Low Bill Rates, 100th AES Convention, Copenhagen (May 1996).

Frank Baumgarte, Charalampos Ferekidis, and Hendrik Fuchs, A Nonlinear Psychoacoustic Model Applied to the ISO MPEG Layer 3 Coder, 99th AES Convention, New York (Oct. 1995).

Lawrence T. Cohen, Louise M. Richards, Elaine Saunders, and Robert S.C. Cowen, Spatial Spread of Neural Excitation in Cochlear Implant Recipients: Comparison of Improved ECAP Method and Psychophysical Forward Masking, 179 Hearing Res. 72-87 (May 2003).

Abbas PJ, Brown CJ, Hughes ML, Ganz BJ, Wolaver AA, Gervais JP and Hong SH, Electrically evoked compound action potentials recorded from subjects who use the nucleus C124M device, 185 Ann Otol Rhinol Laryngol Suppl. 6-9 (Dec 2000).

Lawrence T. Cohen, Elaine Saunders, and Louise M. Richardson, Spatial Spread of Neural Excitation: Comparison of Compund Action Potential and Forward-Masking Data in Cochlear Implant Recipients, 43 International Journal of Audiology.

Miller CA, Abbas PJ, Brown CJ, An Improved Method of Reducing Stimulus Artifact in the Electrically Evoked Whole Nerve Potential 21(4) Ear Hear 280-90 (Aug. 2000).

International Search Report dated Oct. 5, 2001; counterpart patent application PCT/AU01/01032 filed Aug. 21, 2001; Publication No. WO 02/17679; Publication Date Feb. 29, 2002: Inventors: John Parker et al.: Applicant Cochlear Limited.

International Preliminary Examination Report dated Apr. 10, 2002; counterpart patent application PCT/AU01/01032 filed Aug. 21, 2001; Publication No. WO 02/17679; Publication Date Feb. 28, 2002: Inventors: John Parker et al.: Applicant Cochlear Limited.

Supplemental European Search Report dated Aug. 11, 2005.

Japanese Patent Application No. 2002-561453, Notice of Reasons for Rejection dated Jun. 16, 2009. (English Translation).

"Specialty Coating Systems: Rubber/Silicone", Specialty Coating Systems, (Webpage), www.scscoatings.com/1 parylene_applications/rubber-silicone.cfm, accessed via Internet Archive Wayback Machine (archive.org), available Nov. 24, 2005 (based on records of Internet Archive).

* cited by examiner

POWER EFFICIENT ELECTRICAL STIMULATION

CROSS-REFERENCE TO RELATED APPLICATIONS

This application is a continuation of U.S. patent application Ser. No. 10/343,397, filed Feb. 21, 2003, now U.S. Pat. No. 7,272,446 which was a National Stage application of International Application PCT/AU01/01032, filed Aug. 21, 2001, and which claims the benefit of Australian Patent Application PQ 9528, filed Aug. 21, 2000, all of which are hereby incorporated by reference herein.

TECHNICAL FIELD

The present invention relates to devices and methods for neural stimulation, and particularly but not exclusively to auditory prostheses.

BACKGROUND ART

Wearable medical devices reliant upon stored power share a common dynamic. As the possible and desired functionality of the devices is improved, the power demands generally also increase. As a result, the life per charge or per cell is reduced, which has not only a cost impact for the user, but also increases the risk that a device will power down at an inconvenient time.

In the field of cochlear implants, this issue is exacerbated by the trend to a single, behind the ear unit to replace what was once a head mounted unit and a separate speech processor unit worn on the body. The available volume and weight for the power cell is accordingly reduced. Increased power demands to provide improved functionality create a need to consider the efficiency of speech processing schemes and stimulus sets in order to provide maximum battery life.

It is an object of the present invention to provide an improved processing method and device, in order to a better balance of power consumption and performance in neural stimulation systems, particularly auditory prostheses.

SUMMARY OF THE INVENTION

The present invention provides, broadly, for a scheme in which masking effects are taken into account when determining which stimuli are actually delivered to a patient. This may be implemented in various ways. In one approach, after a set of stimulus instructions is generated, the set is checked against a look-up table. This table contains combinations of stimuli which have previously been clinically determined for that patent to display a masking effect. The second stimulus is deleted in this case.

In another approach, a theoretical model of masking could be used in addition to or instead of a look up table.

According to one aspect, the present invention relates to a method of neural stimulation of the type in which successive stimuli are presented on an electrode array having one or more electrodes, said stimuli being generated by a stimulus generation device, the method including the steps of:
  determining a stimulus set for one or more periods;
  analysing each proposed stimulus set using a predetermined instruction set which is adopted to locate factors indicative of a likely masking effect;
  if masking effects are detected, altering said stimulus set for one or more of said periods;
  presenting the stimuli via said electrode array to a neural structure.

According to another aspect, the present invention provides a neural stimulator device, including a stimulus generation device for generating stimulus sets for one or more periods, said stimulus sets being intended for delivery at an electrode array for operatively presenting stimuli to neural structures,
  wherein said device further includes processing means implementing a predetermined instruction set, said processing means analysing each stimulus set using said predetermined instruction set in order to locate factors indicative of a likely masking effect, and if it is determined that a masking effect is likely, altering said stimulus set.

The stimulus set may include a single stimulus in which case only the variable parameters relevant to that type of stimulation need to be specified. In suitable devices, this may include the timing, waveform, frequency, current, voltage, phase, amplitude and electrode location or further factors as required. The instruction set in this case preferably will consider the stimuli previously delivered in determining whether a masking effect is likely.

Alternatively, the stimulus set may include multiple stimuli, with variables as discussed above. If this case, in addition to or instead of previous stimulus sets, the instruction set will preferably analyse the various stimuli in relation to each other.

The stimulus generation device may be unitary or be made of physically distinct parts. For example, in the case of a cochlear implant, it may include both an external speech processor and an implanted device, only the speech processor, or only an implanted device, depending upon the desired location of processing capacity. The instruction set may be implanted as a separate procedure, or integrated within the processor which generates the stimulus set.

In a preferred form, if analysis indicates a likelihood of masking, the masked stimulus is simply omitted. However, in a system such as a cochlear implant, where stimuli are presented on multiple electrodes, an alternative stimuli—for example, on a different electrode—may be substituted. For example, the next most significant sound channel may be selected as the basis for stimulation.

In the case of the intra-cochlear implant, it has been observed that certain stimuli, when delivered simultaneously or in close succession, do not produce a patient percept significantly different from when only the first stimulus is delivered. For example, consider a conventional, multi-electrode intra-cochlear electrode array. If a large amplitude stimulus is delivered at one electrode, and simultaneously a smaller amplitude stimulus is delivered at the next electrode, then in many cases the user will not be able to perceive whether or not the smaller stimulus was delivered—it is said to be masked by the large stimulus. Other circumstances may give rise to masking of various neural percepts. Masking phenomena have been discussed in the technical literature.

The present invention arises from a recognition that masking effects can be considered as indicating a waste of stimulation power, as although the stimulus is presented to the patient, the patient does not receive any increased perception as a result of the stimulus. Accordingly, a proportion of the stimulus energy is simply wasted.

BRIEF DESCRIPTION OF DRAWINGS

An implementation of the present invention will now be described with reference to the accompanying figures, in which.

The present invention will be described with particular reference to a speech processor unit for a cochlear implant system. However, it will be appreciated that the present invention has application to other neural stimulation systems where the masking phenomenon may be relevant.

Figure 1:
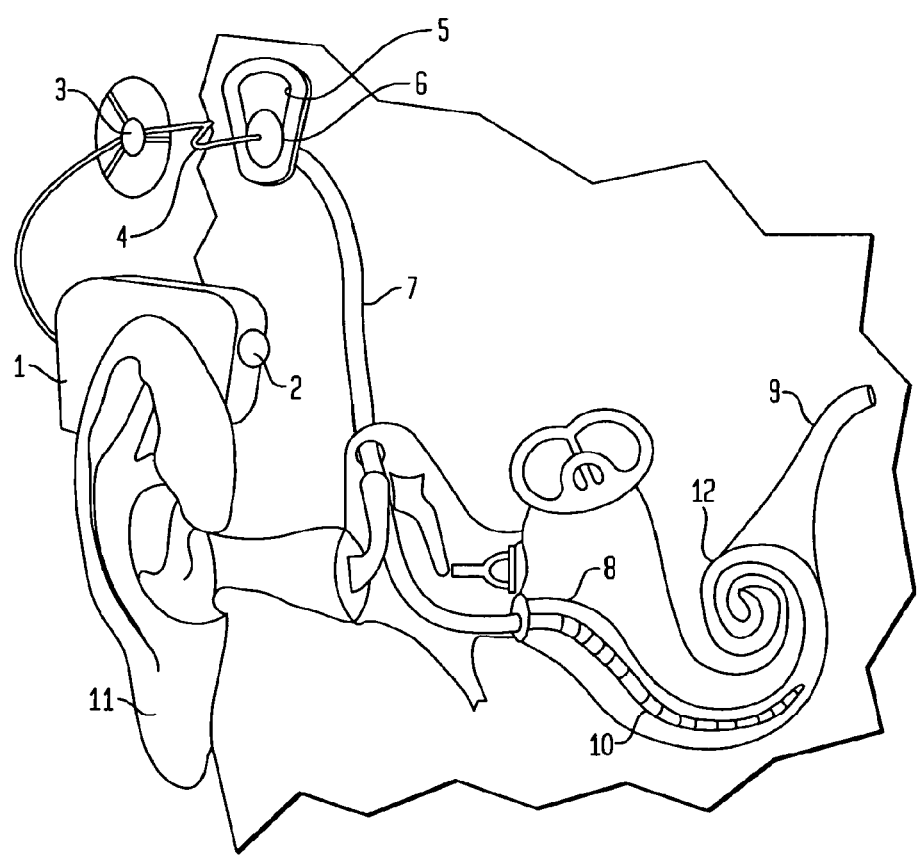
FIG. 1 is a schematic illustration of a conventional intra-cochlear implant system.

Referring to FIG. 1, a typical cochlear implant device is shown. The external component, includes a speech processor 1, and a microphone 2. The speech processor is in this illustration constructed and arranged so that it can fit behind the outer ear 11. Attached to speech processor 1 is a transmitter coil 3 which transmits the electrical signals to the implanted unit 5 via an RF link 4.

The implanted component 5 includes a receiver coil 6 for receiving power and data from coil 3. A cable 7 extends from the implanted device 5 to the cochlea 12 and terminates in an electrode array 10. The signals thus received are applied by the array 10 to the basilar membrane 8 thereby stimulating the auditory nerve. The operation of the device shown in FIG. 1 is described, for example, in U.S. Pat. No. 4,532,930.

Thus, the RF link, which is in turn powered by the speech processor 1, provides power and data to the implanted device 6. The speech processor also processes sound signals received by microphone 2, so as to send appropriate instructions for stimulation to the implanted device 6. The precise details of speech processing are not necessary for an understanding of the present invention, and are in any case well understood by those skilled in the art. Any suitable speech processing strategy could be used in conjunction with the present invention.

Figure 2:
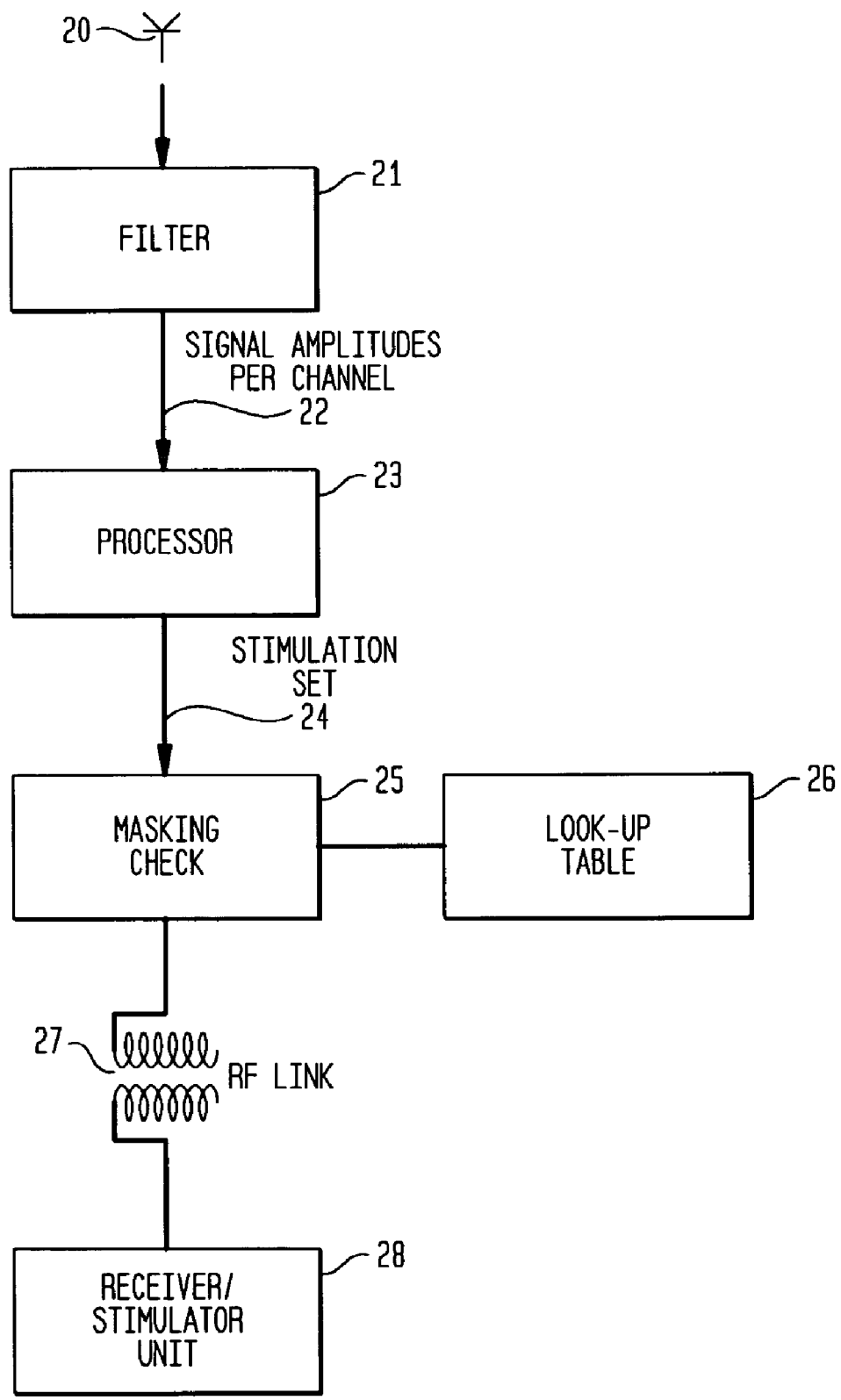
FIG. 2 is a block diagram illustrating the operation of one embodiment of the inventive system.

The block diagram of FIG. 2 illustrates one implementation of the present invention, in schematic terms.

Sound signals are detected by microphone 20, and processed into a predetermined number of frequency channels by filter 21. The output of filter 21 is a set of signal amplitudes per channel 22. Processor 23, in simple terms, selects certain channels as the basis for stimulation, based on amplitude or other factors. A set of stimulation instructions for implanted receiver stimulator unit 28 is thereby produced.

These instructions include at least the electrode or electrodes to be stimulated, and the amplitude of the stimulus to be applied. The process so far is conventional.

Masking check involves comparing each successive two or more stimuli with the look-up table to determine whether they match a predetermined masking rule in look-up table 26.

The table below sets out a set of minimum unmasked level—that is, for one electrode n, the level which will not be masked, as a function of the stimulus levels which have been applied to the other electrodes within the previous $2m^5$. The electrode column lists the electrodes in an array of n max electrodes. Each entry M gives the minimum stimulus level (amplitude) to electrode n which will elicit a response immediately following a stimulus to the relevant electrodes, expressed as values between threshold (T) and maximum comfortable (c) levels. It will be appreciated that T and C levels are routinely determined during set up of a speech processor.

| Minimum Unmasked Level | |
|---|---|
| Electrode | |
| 1 | $M_{1, T} M_{1, T+1} --- M_{1, c-1} M_{1, C}$ |
| 2 | |
| \| | |
| \| | |

| Minimum Unmasked Level | |
|---|---|
| Electrode | |
| n − 1 | $M_{n-1, T} M_{n-1, T+1} --- M_{n-1, C}$ |
| n − 1 | |
| \| | |
| \| | |
| \| | |
| \| | |
| N max | |

The masking check output is thus the stimulation set, with masked stimuli excluded. This is then transmitted conventionally, for example via an RF link to the implanted receiver/stimulator unit, which operates conventionally.

Variations and additions will be apparent to those skilled in the art with the broad scope of the present invention.

The invention claimed is:

1. A neural stimulator device for electrically stimulating a recipient, comprising:
    a stimulus generation device configured to determine a stimulus set of electrical stimuli;
    a processor configured to analyze said stimulus set to determine if any of said stimuli are likely to be masked upon delivery of the stimulus set to the recipient, and to delete one or more of said stimuli likely to be masked; and
    an electrode array configured to deliver the stimulus set to the recipient.

2. The device of claim 1, wherein the processor is further configured to add at least one alternative stimuli to said stimulus set if likely masked stimuli are deleted.

3. The device of claim 2, wherein said electrode array comprises a plurality of electrodes, wherein each of said stimuli of said stimulus set are configured to be presented via one of said plurality of electrodes, and wherein the processor is further configured to delete at least one stimuli configured to be presented via a first electrode, and to add a new stimuli corresponding to the deleted stimuli for presentation via a second electrode.

4. The device of claim 1, wherein said processor is configured to utilize a look-up table to determine if any of said stimuli are likely to be masked.

5. The device of claim 1, wherein said processor is configured to utilize a theoretical masking model to determine if any of said stimuli are likely to be masked.

6. The device of claim 1, wherein said stimulus generation device is configured to determine a plurality of stimulus sets each comprising electrical stimuli, and wherein said processor is configured to analyze a selected stimulus set in relation to a previously determined stimulus set to determine if any of said one or more stimuli in said selected set are likely to be masked.

7. The device of claim 1, wherein said stimulus generation device is configured to determine a stimulus set comprising a plurality of stimuli, and wherein said processor is configured to analyze said plurality of stimuli in relation to one another to determine if any of said plurality of stimuli are likely to be masked.

8. A neural stimulation system, comprising:
    means for determining a stimulus set comprising electrical stimuli;
    processing means for analyzing said stimulus set to determine if any of said stimuli are likely to be masked upon delivery of the set to the recipient;

means for deleting at least one of said likely masked stimuli; and means for presenting the stimulus set to the recipient.

9. The system of claim 8, wherein the system further comprises:

means for adding at least one alternative stimuli to said stimulus if likely masked stimuli are deleted.

10. The system of claim 9, wherein said means for presenting the stimulus set to the recipient comprises an implantable electrode array, wherein said stimuli of said stimulus set are configured to be presented via one of a plurality of electrodes of said implantable electrode array, and wherein the system further comprises:

means for deleting at least one stimuli configured to be presented via a first electrode; and means for adding a new stimuli corresponding to the deleted stimuli for presentation via a second electrode.

11. The system of claim 8, wherein said means for analyzing said stimulus set comprises:

means for utilizing a look-up table to determine if any of said stimuli are likely to be masked.

12. The system of claim 8, wherein said means for analyzing said stimulus set comprises:

means for utilizing a theoretical masking model to determine if any of said stimuli are likely to be masked.

13. The system of claim 8, wherein said means for determining a stimulus set comprising electrical stimuli further comprises:

means for determining a plurality of stimulus sets each comprising electrical stimuli.

14. The system of claim 13, wherein said means for analyzing said stimulus set further comprises:

means for analyzing a selected stimulus set with a previously determined stimulus set to determine if any of said stimuli are likely to be masked.

15. The system of claim 8, wherein said determined stimulus set comprises a plurality of stimuli, and wherein said means for analyzing said stimulus set comprises:

means for analyzing said plurality of stimuli in said determined stimulus set in relation to one another to determine if any of said plurality of stimuli are likely to be masked.

16. A neural stimulator device for electrically stimulating a recipient, comprising:

a stimulus generation device configured to determine a stimulus set comprising one or more electrical stimuli;

a processor configured to analyze said stimulus set to determine if any of said one or more stimuli are likely to be masked upon delivery of the set to the recipient, and to delete at least one of said one or more stimuli in said stimulus set if masking effects are detected; and an electrode array configured to deliver the stimulus set to the recipient.

17. The device of claim 16, wherein the processor is further configured to add at least one alternative stimuli to said stimulus set if masking effects are detected.

18. The device of claim 17, wherein said electrode array comprises plurality of electrodes, wherein each of said one or more stimuli of said stimulus set are configured to be presented via one of said plurality of electrodes, and wherein the processor is further configured to delete at least one stimuli configured to be presented via a first electrode, and to add said deleted stimuli for presentation via a second electrode.

19. The device of claim 16, wherein said processor is configured to utilize a look-up table containing combinations of stimuli previously clinically determined to display a masking effect to determine if any of said one or more stimuli are likely to be masked.

20. The device of claim 16, wherein said processor is configured to utilize a theoretical masking model to determine if any of said one or more stimuli are likely to be masked.

21. The device of claim 16, wherein said stimulus generation device is configured to determine a plurality of stimulus sets each comprising one or more stimuli, and wherein said processor is configured to analyze said stimulus set in relation to a previously determined stimulus set to determine if any of said one or more stimuli are likely to be masked.

22. The device of claim 16, wherein said stimulus generation device is configured to determine a stimulus set comprising a plurality of stimuli, and wherein said processor is configured to analyze said plurality of stimuli in relation to one another to determine if any of said plurality of stimuli are likely to be masked.

* * * * *